United States Patent [19]

Tyson

[11] Patent Number: Plant 5,655

[45] Date of Patent: Feb. 4, 1986

[54] PEACH TREE—TYSON 820 CULTIVAR

[75] Inventor: J. D. Tyson, Monroe, N.C.

[73] Assignee: Stark Brothers Nurseries & Orchards Co., Louisiana, Mo.

[21] Appl. No.: 594,551

[22] Filed: Mar. 29, 1984

[51] Int. Cl.[4] ..... A01H 5/03

[52] U.S. Cl. ..... Plt./43

[58] Field of Search ..... Plt./43

*Primary Examiner*—Robert E. Bagwill

*Attorney, Agent, or Firm*—Burns, Doane, Swecker & Mathis

[57] ABSTRACT

A new and distinct peach tree variety of chance seedling origin is provided. This new variety is a very late maturing yellow freestone peach variety which bears abundant, regular crops of large round meaty fruit having an attractive red and yellow skin coloration. The fruit flesh has a mild and delicious flavor and is of a rich yellow color which resists browning when exposed to air. The fruit buds exhibit superior winter hardiness. Also, the variety has exhibited tolerance to major peach diseases common to the southeastern portion of the United States.

1 Drawing Figure

SUMMARY OF THE INVENTION

The new and distinct variety of peach tree originated in the cultivated state in my orchard at Monroe, N.C., as a chance seedling in a 1975 planting of Louisiana Surecrop peach trees budded to Lovell seedling rootstock. The present variety was derived from a shoot which is believed to have developd from one of the seedling rootstocks.

In 1978 the present variety was noted during its first year of bearing because of its abundant production of large very late-maturing peaches. Continued observation of this variety has convinced me that it is a new and distinct variety.

I have observed at various test orchard locations that the present variety is large, vigorous, and upright, and has a chilling requirement of approximately 850 hours. In orchards at Monroe, N.C., the new variety has exhibited exceptional winter hardiness by cropping well while other adjacent standard varieties have produced no fruit due to the loss of blossom buds caused by winter freezing. At the Sandhills Research Station of North Carolina State University at Jackson Springs, N.C., the present variety was observed not to become infected by common bacterial leaf spot (causal organism, *Xanthomonas pruni* E. F. Smith) under conditions favorable to the development of this disease.

The new variety of the present invention is distinguishable by the abundant production of high quality fruit very late in the peach harvest season. The fruit is produced approximately 18 to 20 days after that of the Elberta variety, and approximately 8 to 10 days after that of the Rio Oso Gem variety (U.S. Plant Pat. No. 84). The fruit is above average in size, possesses a very attractive red-blush over a yellow ground color, is of good eating quality, and is notable because the yellow meaty flesh will not brown when cut and exposed to air as is common with other peach varieties.

Asexual propagation of the new variety on my behalf by budding in 1979 at the Sandhills Research Station, Jackson Springs, N.C., and subsequent observation by me has demonstrated that its combination of characteristics comes true to form and is established and is transmitted through succeeding propagation. All specimens described herein were grown in Union County, N.C.

The new variety has been named the TYSON 820 cultivar and is being marketed by Stark Brothers Nurseries & Orchards Company under the STARK and FINALE trademarks.

BRIEF DESCRIPTION OF THE PHOTOGRAPH

The accompanying photograph shows typical specimens of the fruit and foliage of the new variety in color as nearly true as it is reasonably possible to make the same in a color illustration of this character.

DETAILED DESCRIPTION OF NEW VARIETY

The following is a detailed description of the new variety where color terminology is to be accorded its ordinary dictionary significance except where otherwise indicated. The specimens described were grown at Monroe, Union County, N.C. The characteristics were observed for a mature 8 year-old tree.

Representative dates of first and last pickings at Union County, N.C. are Aug. 18, and Aug. 21, 1981.

Tree: Large size; vigorous; upright; medium dense; very productive; regular bearing.

*Trunk.*—Size. — Medium. Texture. — Medium rough.

*Branches.*—Size — Medium. Texture — Medium Color — Greyish brown to brown. Lenticels — Medium large in size; medium in number.

*Leaves.*—Size — Medium; average length approximately $6\frac{3}{4}$ inches; average width approximately $1\frac{1}{2}$ inches. Shape — Lanceolate; acute apex; acute base. Texture — Upper surface smooth; lower surface smooth with raised veins. Color — Upper Surface — Forest Green, Plate XVII 29 m, Ridgway Color Standards and Nomenclature. Color — Under Surface — Bice Green, Plate XVII 29 k, Ridgway Color Standards and Nomenclature. Margin — Crenate. Petiole — Short, average length approximately $\frac{3}{8}$ inch. Glands — Medium small, reniform, approximately 4 to 7 in number, most often 6 in number, located on lower leaf margin and upper portion of petiole.

Flowers: Early; light pink to very nearly white, large and showy; pollen is present.

Fruit: Maturity when described — Eating ripe, date — Aug. 29, 1983.

*Size.*—Large, uniform. Axial diameter — Approximately $2\frac{3}{4}$ to 3 inches. Transverse in suture plane — Approximately $2\frac{7}{8}$ to $3\frac{1}{8}$ inches. At right angle to suture plane — Approximately $2\frac{7}{8}$ to 3 inches.

*Form.*—Globose, uniform, very nearly symmetrical.

*Suture.*—Narrow and shallow, continues from apex to base.

*Ventral surface.*—Rounded and equal.

*Cavity.*—Rounded, obtuse, approximately $\frac{3}{8}$ inch deep and approximately 1 inch wide.

*Base.*—Rounded.

*Apex.*—Rounded, with a very slight depression containing a very small tip.

*Skin.*—Medium thickness, tenacious to flesh no tendency to crack in wet season, slight tendency to crack in dry season, scant and short down. Color — Ground color is straw yellow, Plate XVI 21d, Ridgway Color Standards and Nomenclature with an approximately 60 to 70 percent red blush which is Dragon's-blood-Red, Plate XIII 5k, Ridgway Color Standards and Nomenclature.

*Flesh.*—Color — Antimony Yellow, Plate XV 17b, Ridgway Color Standards and Nomenclature, mottled with red next to the pit, the surface of the pit cavity is red with white blotching. Texture — Meaty. Juice — Moderate. Ripens — Uniformly. Flavor — Subacid to mild. Fibers — Few and fine. Aroma — Distinct. Eating quality — Good, flesh is substantially non-browning upon exposure to air.

*Stone.*—Freestone; parts smoothly from the flesh. Size — Medium, average length approximately $1\frac{1}{2}$ inch and average thickness approximately $\frac{7}{8}$ inch. Base — Hilum. Apex — Accuminate. Sides — Nearly equal. Surface — Regularly furrowed throughout. Color — Prout's Brown, Plate XV 15 m, Ridgway Color Standards and Nomenclature.

Use: Local and long distance market, dessert.

Keeping quality: Good.

Shipping quality: Good.

I claim:

1. A new and distinct variety of peach tree, substantially as illustrated and described, characterized by (a) a large and vigorous growth habit, (b) the exceptional winter hardiness of fruit buds, and (c) the ability to regularly and abundantly yield large very late maturing fruit of good quality having an attractive red and yellow skin coloration and a meaty substantially non-browning yellow flesh which possesses good eating and shipping qualities.

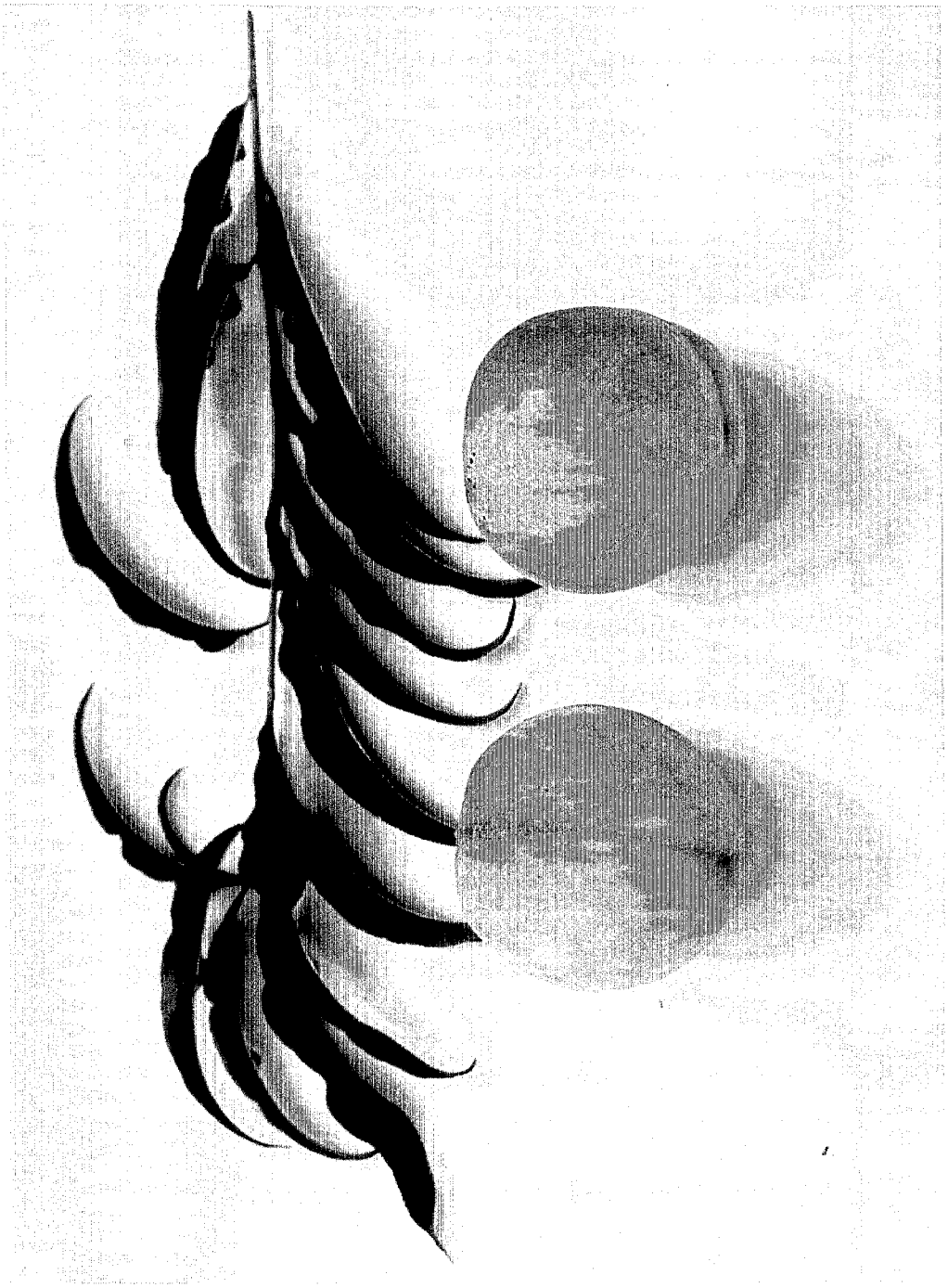

* * * * *